US00PP36421P2

(12) United States Plant Patent
d'Hont et al.

(10) Patent No.: US PP36,421 P2
(45) Date of Patent: Feb. 4, 2025

(54) STRAWBERRY PLANT NAMED 'Ravellia'

(50) Latin Name: ***Fragaria* x *ananassa***
Varietal Denomination: Ravellia

(71) Applicant: FRESH FORWARD HOLDING B.V., Huissen (NL)

(72) Inventors: Rob Peter Edith d'Hont, Doorwerth (NL); Egbertus Joseph Meulenbroek, Zetten (NL)

(73) Assignee: FRESH FORWARD HOLDING B.V., Huissen (NL)

( * ) Notice: Subject to any disclaimer, the term of this patent is extended or adjusted under 35 U.S.C. 154(b) by 0 days.

(21) Appl. No.: 18/634,931

(22) Filed: Apr. 13, 2024

(51) Int. Cl.
*A01H 5/08* (2018.01)
*A01H 6/74* (2018.01)

(52) U.S. Cl.
USPC ..... Plt./208

(58) Field of Classification Search
USPC ..... Plt./208, 209
See application file for complete search history.

*Primary Examiner* — Susan McCormick Ewoldt
(74) *Attorney, Agent, or Firm* — C. Anne Whealy

(57) ABSTRACT

A new and distinct cultivar of Strawberry plant named 'Ravellia', characterized by its upright plant habit; vigorous growth habit; mid-season flowering; uniform and mid-season fruit ripening; medium to large conical fruits that are glossy and bright red in color; pleasant fruit aroma and rich in sweetness and acidity; and excellent fruit postharvest longevity.

3 Drawing Sheets

Figure 1:
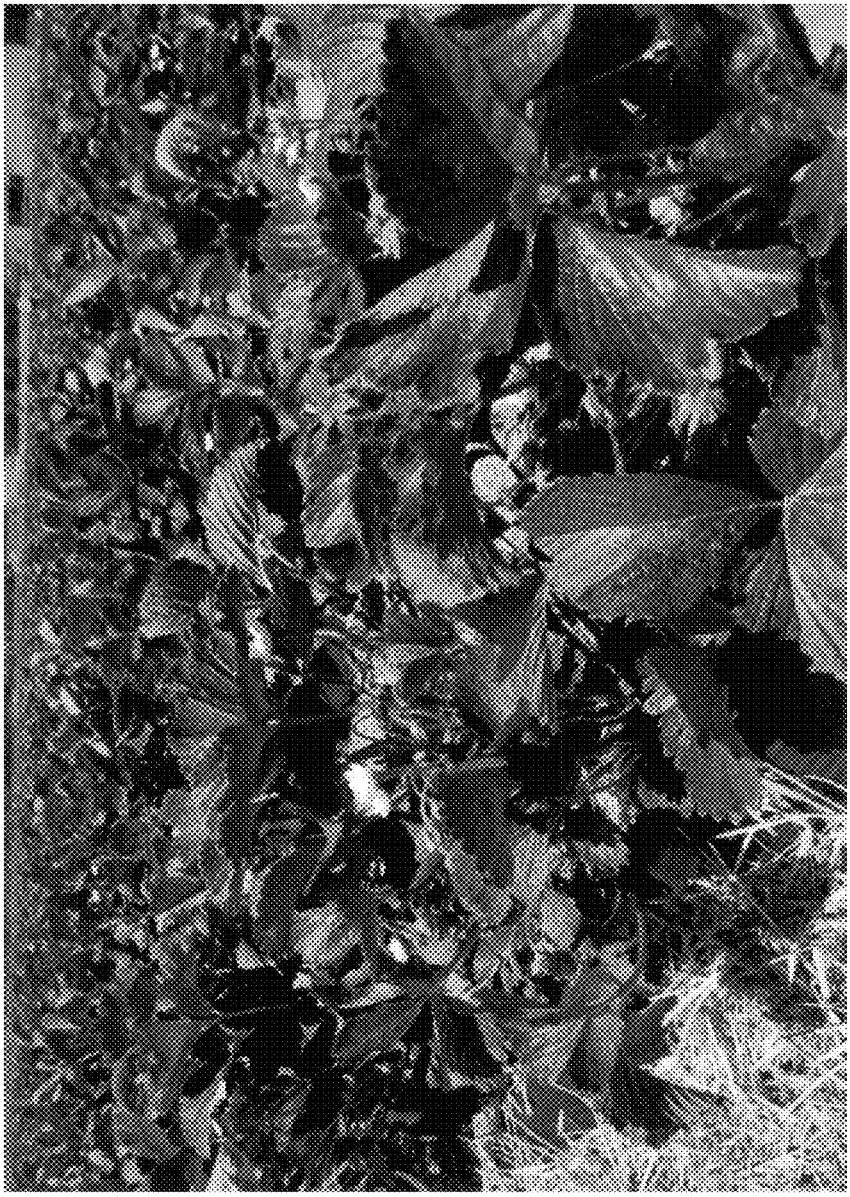

Botanical designation: *Fragaria* x *ananassa*.
Cultivar denomination: 'RAVELLIA'.

CROSS-REFERENCED TO CLOSELY-RELATED APPLICATIONS

Title: Strawberry Plant Named 'Cadenza'
Inventors: Rob Peter Edith d'Hont & Bert Meulenbroek
Filed: Concurrently with the instant application

STATEMENT REGARDING PRIOR DISCLOSURES BY INVENTORS & APPLICANT/ASSIGNEE

A Plant Breeder's Rights application in the European Community for the instant plant was filed by the Applicant/Assignee, Fresh Forward Holding B.V. of Huissen, The Netherlands on Sep. 13, 2021, application number 2021/2251. Foreign priority is claimed to this application.

A Plant Breeder's Rights application in the United Kingdom for the instant plant was filed by the Applicant/Assignee, Fresh Forward Holding B.V. of Huissen, The Netherlands on Sep. 13, 2021, application number XU_302022000_01044. Foreign priority is claimed to this application.

A Plant Breeder's Rights application in Norway for the instant plant was filed by the Applicant/Assignee, Fresh Forward Holding B.V. of Huissen, The Netherlands on Sep. 12, 2021, application number 1767. Foreign priority is claimed to this application.

A Plant Breeder's Rights application in Switzerland for the instant plant was filed by the Applicant/Assignee, Fresh Forward Holding B.V. of Huissen, The Netherlands on Sep. 9, 2021, application number 22-3538. Foreign priority is claimed to this application.

The Inventors and Applicant/Assignee assert that no sales, offers for sale or public distribution of the instant plant occurred more than one year prior to the effective filing date of this application.

Any information about the claimed plant would have been obtained from a direct or indirect disclosure from the Inventors and/or Applicant/Assignee. Inventors and Applicant/Assignee claim a prior art exception under 35 U.S.C. 102(b)(1) for disclosures and/or sales prior to the filing date but less than one year prior to the effective filing date.

BACKGROUND OF THE INVENTION

The present Invention relates to a new and distinct cultivar of Strawberry plant, botanically known as *Fragaria* x *ananassa* and hereinafter referred to by the name 'Ravellia'.

The new Strawberry plant is a product of a planned breeding program conducted by the Inventors in Gelderland and Stevensbeek, The Netherlands. The objective of the breeding program was to develop new Strawberry plants with good fruit quality, ease of harvesting, high yield, large attractive fruits and good postharvest longevity.

The new Strawberry plant originated from a cross-pollination by the Inventors in April 2016 in Gelderland, The Netherlands of a proprietary selection of *Fragaria* x *ananassa* identified as code number E2012-1189, not patented, as the female, or seed, parent with a proprietary selection of *Fragaria* x *ananassa* identified as code number E2008-002, not patented, as the male, or pollen, parent. The new Strawberry plant was discovered and selected by the Inventors as a single plant from within the progeny of the stated cross-pollination in a controlled environment in Stevensbeek, The Netherlands in July 2018.

Asexual reproduction of the new Strawberry plant by runner cuttings in a controlled environment in Gelderland, The Netherlands since September 2018 has shown that the unique features of this new Strawberry plant are stable and reproduced true to type in successive generations of asexual reproduction.

SUMMARY OF THE INVENTION

Plants of the new Strawberry have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Ravellia'. These characteristics in combination distinguish 'Ravellia' as a new and distinct Strawberry plant:

1. Upright plant habit.
2. Vigorous growth habit.
3. Mid-season flowering.
4. Uniform and mid-season fruit ripening.
5. Medium to large conical fruits that are glossy and bright red in color.
6. Pleasant fruit aroma and rich in sweetness and acidity.
7. Excellent fruit postharvest longevity.

Plants of the new Strawberry differ primarily from plants of the female parent selection in the following characteristics:

1. Fruits of plants of the new Strawberry are conical in shape whereas fruits of plants of the female parent selection are cordate in shape.
2. Fruits of plants of the new Strawberry are darker red in color than fruits of the female parent selection.
3. Calyces of plants of the new Strawberry are not as inserted into the fruit than calyces of plants of the female parent selection.

Plants of the new Strawberry differ primarily from plants of the male parent selection in the following characteristics:

1. Leaves of plants of the new Strawberry are lighter green in color than leaves of plants of the male parent selection.
2. Fruits of plants of the new Strawberry are conical in shape whereas fruits of plants of the male parent selection are cordate in shape.
3. Fruits of plants of the new Strawberry are lighter red in color than fruits of the male parent selection.

Plants of the new Strawberry can be compared to plants of *Fragaria* x *ananassa* 'Cadenza', disclosed in U.S. Plant Patent application filed concurrently. In side-by-side comparisons, plants of the new Strawberry differ primarily from plants of 'Cadenza' in the following characteristics:

1. Plants of the new Strawberry flower and produce fruit earlier than plants of 'Cadenza'.
2. Fruits of plants of the new Strawberry are bright red in color whereas fruits of plants of 'Cadenza' are orangish red in color.

Plants of the new Strawberry can be compared to plants of *Fragaria* x *ananassa* 'Jive', disclosed in U.S. Plant Pat. No. 26,711. In side-by-side comparisons, plants of the new Strawberry differ primarily from plants of 'Jive' in the following characteristics:

1. Plants of the new Strawberry are taller and more upright than plants of 'Jive'.
2. Plants of the new Strawberry flower and produce fruit earlier than plants of 'Jive'.
3. Fruits of plants of the new Strawberry are darker red in color than fruits of plants of 'Jive'.
4. Plants of the new Strawberry have larger sepals than plants of 'Jive'.

Plants of the new Strawberry can also be compared to plants of *Fragaria* x *ananassa* 'Elsanta', not patented. In side-by-side comparisons, plants of the new Strawberry differ primarily from plants of 'Elsanta' in the following characteristics:

1. Plants of the new Strawberry are taller and more upright than plants of 'Elsanta'.
2. Fruits of plants of the new Strawberry are conical in shape whereas fruits of plants of 'Elsanta' are cordate in shape.

BRIEF DESCRIPTION OF THE PHOTOGRAPHS

The accompanying colored photographs illustrate the overall appearance of the new Strawberry plant showing the colors as true as it is reasonably possible to obtain in colored reproductions of this type. Colors in the photographs may differ slightly from the color values cited in the detailed botanical description which accurately describe the colors of the new Strawberry plant.

The photograph on the first sheet (FIG. 1) is a side perspective view of typical flowering plants of 'Ravellia' grown in a greenhouse environment.

Figure 2:
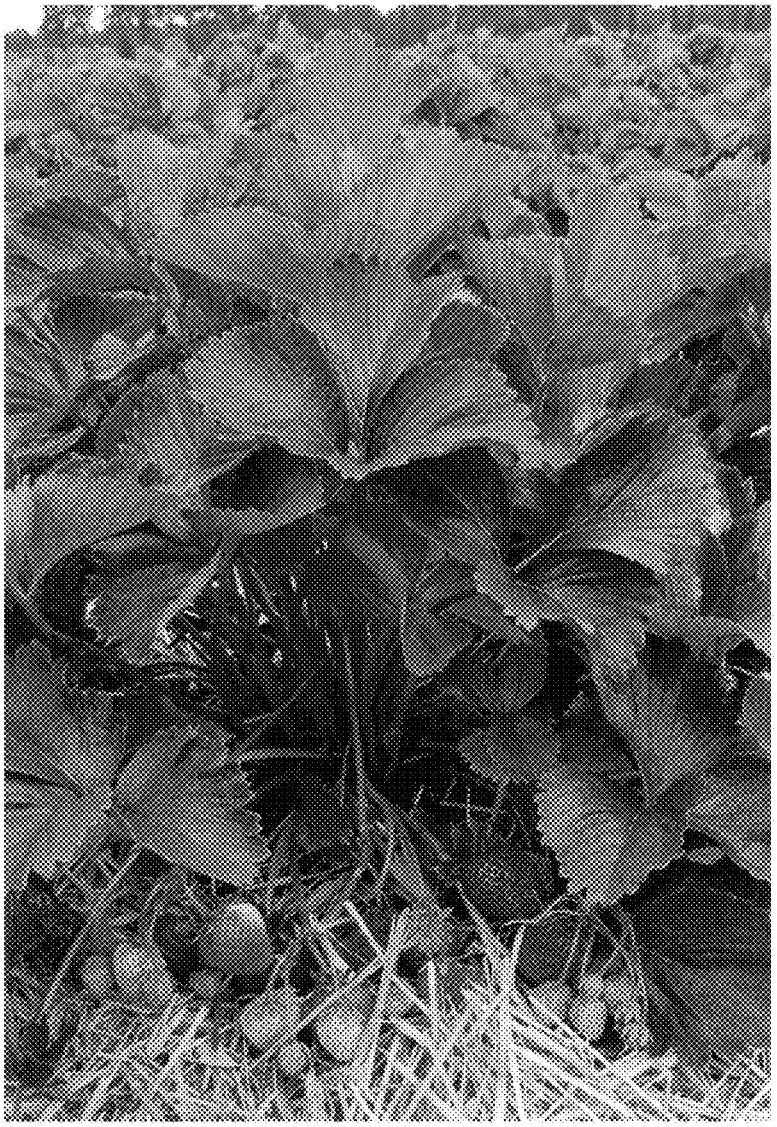
Figure 3:
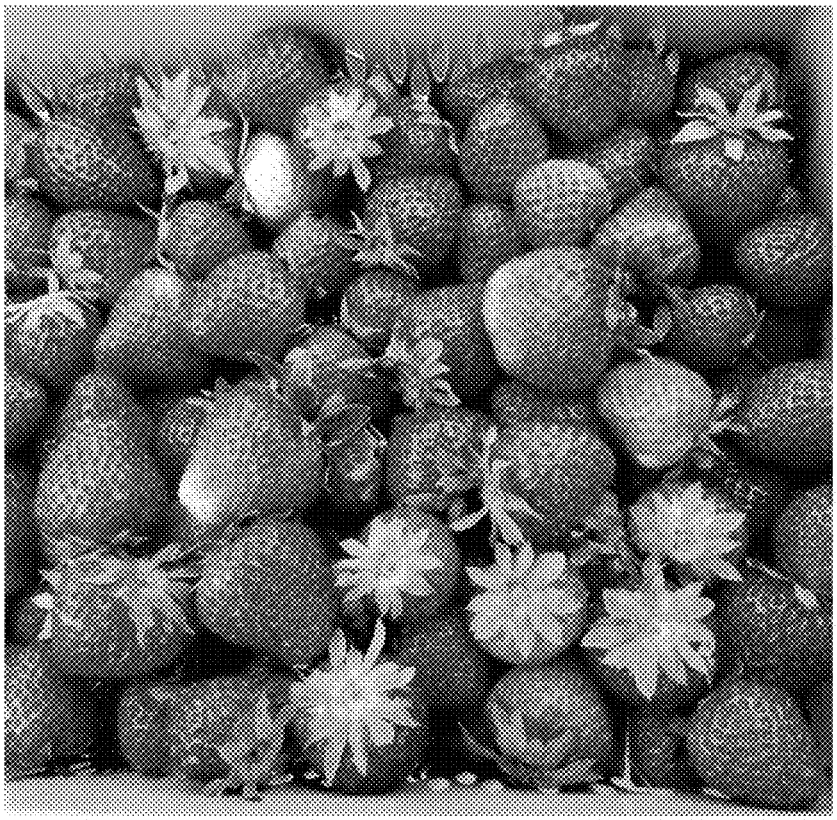

The photograph on the second sheet (FIG. 2) is a side perspective view of typical fruiting plants of 'Ravellia' grown in a greenhouse environment The photograph on the third sheet (FIG. 3) is a close-up view of typical developed fruits of plants of 'Ravellia'.

DETAILED BOTANICAL DESCRIPTION

The following observations and measurements describe plants grown in beds and plants grown in 4.7-liter containers with four plants per container during the winter and spring in a glass-covered greenhouse in Huissen, The Netherlands and under cultural practices typical of commercial Strawberry production. During the production of the plants, day temperatures ranged from 10° C. to 30° C. and night temperatures ranged from 8° C. to 12° C. Plants were one year old when the photographs and the description were taken. In the following description, color references are made to The Royal Horticultural Society Colour Chart, 2001 Edition, except where general terms of ordinary dictionary significance are used.

Botanical classification: *Fragaria* x *ananassa* 'Ravellia'.

Parentage:

*Female, or seed, parent*.—Proprietary selection of *Fragaria* x *ananassa* identified as code designation E2012-1189, not patented.

*Male, or pollen, parent*.—Proprietary selection of *Fragaria* x *ananassa* identified as code designation E2008-002, not patented.

Propagation:

*Type*.—By runner cuttings.

*Time to initiate roots, summer*.—About one to four days at soil temperatures about 15° C. and ambient temperatures about 17° C.

*Time to produce a rooted young plant, summer*.—About two to three weeks at soil temperatures about 15° C. to 20° C. and ambient temperatures about 17° C.

*Root description*.—Medium in thickness, fibrous; typically cream to white in color, actual color of the roots is dependent on substrate composition, water quality, fertilizer type and formulation, substrate temperature and physiological age of roots.

*Rooting habit*.—Moderately freely branching; medium density.

Plant description:

*Plant and growth habit*.—Perennial; upright plant habit; leaves basal; vigorous growth habit and rapid growth rate; density of foliage, medium to dense.

*Plant height*.—About 35 cm to 45 cm.

*Plant diameter*.—About 30 cm to 35 cm.

*Stolon texture*.—Sparsely pubescent.

*Stolon color*.—Close to 144A.

Leaf description:

*Arrangement and appearance*.—Basal rosette; compound with typically three leaflets per leaf; leaflets are not variegated and typically without anthocyanin when grown under normal and healthy growing conditions; to date, blistering has not been observed.

*Leaflet length*.—About 8 cm to 11 cm.

*Leaflet width*.—About 7 cm to 10 cm.

*Leaflet shape*.—Close to rounded to obovate; terminal leaflet concave in cross-section.

*Leaflet apex*.—Obtuse.

*Leaflet base*.—Attenuate to rounded.

*Leaflet margin*.—Serrate to crenate.

*Leaflet texture and luster, upper surface*.—Smooth, glabrous; slightly to moderately glossy.

*Leaflet texture and luster, lower surface*.—Pubescent; matte.

*Leaflet venation*.—Pinnate.

*Leaflet color*.—Developing leaflets, upper surface: Close to 137B. Developing leaflets, lower surface: Close to 138B. Fully expanded leaflets, upper surface: Close to between 137A and 139A; venation, close to 144B to 144C. Fully expanded leaflets, lower surface: Close to 138B; venation, close to 144B to 144C

*Petioles*.—Length: About 15 cm to 35 cm. Diameter: About 4 mm to 6 mm. Texture, upper and lower surfaces: Pubescent; hairs orientated horizontally. Color, upper and lower surfaces: Close to 145A.

Flower description:

*Flower form and flowering habit*.—Rotate flowers arranged singly at lateral apices; flowers held mostly upright; flowers are self- fertile; about 40 to 70 flowers develop per plant.

*Fragrance*.—None detected.

*Natural flowering season*.—Mid-season flowering habit; in the greenhouse, plants flower from early March to late March and in outdoor production, plants flower from mid-April until early May in The Netherlands.

*Flower buds*.—Length: About 1 cm. Diameter: About 1 cm. Shape: Ovoid. Aspect: Mostly upright.

*Flower diameter*.—About 1.5 cm to 2.5 cm.

*Flower depth* (*height*).—About 4 mm to 8 mm.

*Petals*.—Arrangement: Single whorl of five to six petals; petals imbricate. Length: About 8 mm to 12 mm. Width: About 8 mm to 12 mm. Shape: Round to broadly ovate. Apex: Rounded. Base: Obtuse. Margin: Entire. Texture, upper and lower surfaces: Smooth, glabrous; satiny. Color: When opening and fully opened, upper surface: Close to 155D; color does not change with subsequent development. When opening and fully opened, lower surface: Close to 155D; color does not change with subsequent development.

*Sepals*.—Arrangement and calyx description: Single whorl of 10 to 14 sepals; calyx, star-shaped; calyx adherence is level to slightly raised; sepals are orientated downwardly or/and outwardly; calyx diameter is similar to slightly smaller than developed fruit diameter. Calyx length: About 1 cm to 2 cm. Calyx diameter: About 2 cm to 3 cm. Length: About 7 mm to 12 mm. Width: About 5 mm to 7 mm. Shape: Lanceolate to ovate. Apex: Acute. Base: Fused. Margin: Entire. Texture, upper and lower surfaces: Pubescent. Color, upper and lower surfaces: Close to 137A.

*Peduncles*.—Length: About 5 cm to 20 cm. Diameter: About 1 mm to 2 mm. Strength: Strong. Texture: Pubescent; hairs orientated horizontally. Color: Close to 144B.

*Reproductive organs*.—Stamens: Quantity per flower: About 25 to 30. Anther length: About 2 mm. Anther shape: Linear to elliptic. Anther color: Close to 15B. Pollen amount: Abundant. Pollen color: Close to 16B. Pistils: Quantity per flower: About 30. Pistil length: About 1 mm to 2 mm. Stigma shape: Rounded. Stigma color: Close to 6B. Fruits: Quantity per truss: About eight to twelve; fruits are medium to large in size. Time to harvest: Mid-season fruit ripening, fruits; fruits are ready to harvest in early June to late June or early July in The Netherlands; fruit bearing is non-remontant. Postharvest longevity: About seven to ten days at 7° C. Length: About 2 cm to 5 cm. Diameter: About 2 cm to 5 cm. Shape: Conical. Fruit weight per fruit, first quality: About 19.1 g. Fruit weight per plant, first quality: About 1,200 g. Fruit firmness: Firm. Fragrance, taste: Pleasant aroma; very sweet taste. Total titratable acidity and sugar: About 0.77% titratable acidity and about 10% brix. Luster: Uniformly glossy. Surface evenness: Mostly smooth. Color, surface: Close to 45C. Color, flesh: Close to 33A and core, close to 32D. Achene quantity: About 200 to 400 per fruit. Achene position: Slightly inserted. Achene weight: About 0.0067 g. Achene color: Close to 1A. Band width without achenes: If observed, very small.

Pathogen and pest resistance: Plants of the new Strawberry have been observed to be relatively resistant to *Phytophthora cactorum, Sphaerotheca macularis* and *Verticillium dahliae*. To date, plants of the new Strawberry have not been observed to be resistant to pests and other pathogens common to Strawberry plants.

It is claimed:

1. A new and distinct Strawberry plant named 'Ravellia' as herein illustrated and described.

* * * * *